United States Patent [19]
Copes et al.

[11] 3,988,350
[45] Oct. 26, 1976

[54] LOW MOLECULAR WEIGHT SUBSTITUTED PHENOL-LACTAM-SUBSTITUTED PHENOL COMPLEXES FROM LACTAMS AND SUBSTITUTED MONOHYDROXY PHENOLIC COMPOUNDS

[75] Inventors: Joseph P. Copes, Easton, Pa.; David I. Randall, Leland, Mich.

[73] Assignee: GAF Corporation, New York, N.Y.

[22] Filed: Oct. 10, 1974

[21] Appl. No.: 513,874

Related U.S. Application Data

[63] Continuation-in-part of Ser. No. 193,974, Oct. 29, 1971, abandoned.

[52] U.S. Cl. ............................. 260/326.5 FL; 71/88; 71/94; 71/95; 252/106; 252/107; 260/239.3 R; 260/326.5 FN; 260/293.75; 260/293.77; 424/65; 424/244; 424/267; 424/274; 424/358
[51] Int. Cl.² ................ C07D 207/24; C07D 210/00; C07D 211/06
[58] Field of Search ............ 260/239.3 R, 326.5 FL, 260/326.5 FN, 293.75, 293.77

[56] References Cited
OTHER PUBLICATIONS
*J. Org. Chem.*, 29:3122–3124 (1964).

*Primary Examiner*—Frederick E. Waddell
*Attorney, Agent, or Firm*—Walter C. Kehm; Marilyn J. Maue

[57] ABSTRACT

A low molecular weight complex of a lactam and a substituted phenolic compound having the formula

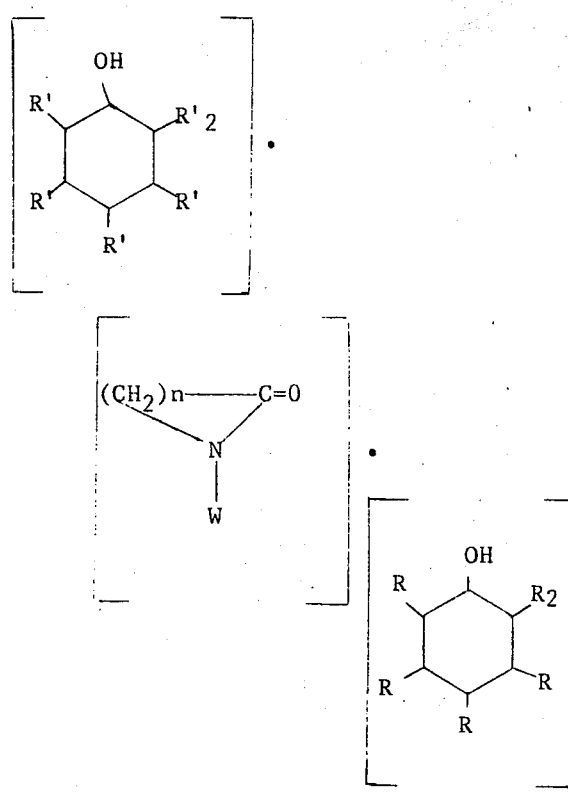

wherein $n$ is an integer of 3 to 5; W is hydrogen or alkyl having from 1 to 8 carbon atoms including cycloalkyl substituents; each R and R', $R_2$ and $R'_2$ is alkoxy of from 1 to 3 carbon atoms, nitro, cyano, hydrogen, halogen or alkyl having from 1 to 12 carbon atoms and at least one R, R', $R_2$ and $R'_2$ is a substituent other than hydrogen, and wherein $R_2$ and $R'_2$ can also be alaninyl.

10 Claims, No Drawings

LOW MOLECULAR WEIGHT SUBSTITUTED PHENOL-LACTAM-SUBSTITUTED PHENOL COMPLEXES FROM LACTAMS AND SUBSTITUTED MONOHYDROXY PHENOLIC COMPOUNDS

This application is a continuation in part of application Ser. No. 193,974, filed Oct. 29, 1971 abandoned herewith, all commonly disclosed subject matter of which is incorporated herein by reference.

The complexes of the invention are useful as germicides, insecticides, wood preservatives, plasticizers, antioxidants and agents permitting the gradual release of various chemicals, such as phenols for use in fertilizers, weed killers, insecticides skin emollients, etc. In regard to agricultural applications, the present compounds are particularly useful in the control of plant diseases and various pests which are known to overwinter and thus provide a constant source of plant infection or infestation.

The present invention relates to relatively low molecular weight complexes of lactams and substituted monohydroxy phenolic compounds. More particularly it is concerned with a low molecular weight crystalline complex having the critical skeletal structure of phenol-lactam-phenol complexes and having a carbonyl infra-red band at 1650cm$^{-1}$ derived from a lactam and the substituted monohydroxy phenol.

It has been postulated that monolactams and other amides form complexes with phenol; however, the prior art is totally lacking in any disclosure or teaching of definitely characterized chemical entities. Thus, for instance, Schmulbach et al (J. Org. Chem. 29, 3122-4, 1964) has reported studies including thermodynamic data based on the addition of phenol to a series of amide solutions including solutions of N-methylvalerolactam, epsiloncaprolactam, N,N-dimethylacetamide, N,N-dimethylpropionamide, N,N-dimethylformamide, N-methylcaprolactam and N-methylpyrrolidone. The reactions were carried out in carbon tetrachloride; however, no actual compounds were isolated or characterized to establish that a complex, as opposed to a chemical mixture, was actually formed. Also characteristics of the products were not determined so that there is no indication of how the products could be usefully employed. Thus, the mixtures of this reference while interesting as chemical curiosities do not have a bearing on the present crystalline complex compounds.

In accordance with the present invention, well defined low molecular weight crystalline complexes having the configuration of phenol-lactam-phenol are derived from a lactam and a substituted monohydroxy phenolic compound.

The complex compounds of the present invention are represented by the structural formula:

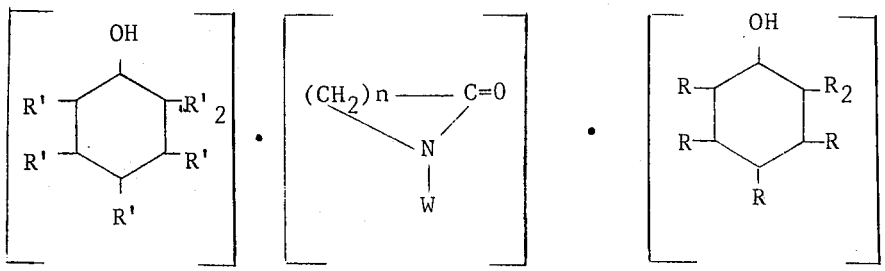

wherein $n$ is an integer of 3 to 5, W is hydrogen or alkyl having from 1 to 8 carbon atoms and includes cycloalkyl substituents eg. cycloalkyl of from 3 to 8, preferably 3 to 6 carbon atoms; each R, R′, R$_2$ and R′$_2$ is hydrogen, alkoxy of from 1 to 3 carbon atoms, nitro, cyano, halogen, or alkyl having from 1 to 12 carbon atoms, preferably 1 to 6 carbon atoms, and at least one substituent of R, R′, R$_2$ and R′$_2$ is a substituent other than hydrogen; and wherein R$_2$ and R′$_2$ can also be alaninyl.

Most preferred of the group of these complexes containing lactam are those wherein the lactam moiety is of the pyrrolidone type; i.e. where n is 3.

The compounds of the foregoing structural formulae can be generally prepared by admixing the lactam and the phenol and isolating the well-defined crystalline complex thereby formed. The complex compounds of this invention are formed in a 2:1 ratio of the phenolic hydroxyl groups to lactam, eg. pyrrolidone or caprolactam.

The lactams of the present invention can be prepared by any of several known methods including the reaction of lactones with ammonia or alkylamine wherein the alkyl group is as defined for W in the above formula. The reaction to form lactam is generally carried out at a temperature between about 150° C and about 325° C. Also, the substituted monohydroxy phenolic compounds employed in this invention can be prepared methods known in the art. In general, nitro groups are added to the phenol ring by reaction with nitric acid; halogens are substituted on the phenol ring by reaction with hydrogen halide or halogen; or by partial fusion of halobenzene (eg. chlorobenzene) with alkali; and cyano groups are substituted by reaction of the phenol with, for example, cyanic acid or by the reaction of a halophenol with cuprous cyanide. Numerous additional methods for preparing the compounds which form the present phenolic moieties are set forth in the art; however, the preparation of these phenolic compounds is not intended to form part of the invention as defined in the appended claims.

In carrying out the complexing reaction of this invention, it is usually advantageous to agitate or agitate and heat the mixture of phenol and lactam, in the presence or absence of a solvent, until a clear, homogenous liquid is obtained, although applied heat may not be desired in every case in view of the exothermic nature of the complexing reaction. More specifically, the complexing reaction can be carried out at a temperature between about room temperature and up to about the boiling point of the complex; although a temperature in excess of 180° C is usually not required. However, in order to obtain a slower rate of reaction and more controlled distribution of the phenolic species with respect to the lactam, temperatures as low as about −10° C can be employed, if desired. The preferred temperature at which the reactants are mixed is within the range of from about room temperature and about 130° C. For the present reaction, there is no preferred order of addition of the reactants to the reaction zone; however, it has been found beneficial to agitate the mixture during the complexing reaction. Usually the reaction takes place in a relatively short period of time, i.e., from a few seconds to a few minutes, most often immediately upon contact of the species in the liquid phase. However, the contacting of lactams and phenolic species may be extended to several hours, about 2 hours, to assure completion. While it is preferred to conduct the reaction under atmospheric pressure, slightly subatmospheric or, in the case of low boiling materials, slightly elevated pressures, from about 10mm Hg to about 25 psig, are also contemplated.

Although stoichiometric amounts, or a slight mol excess of the phenolic compound with respect to lactam is preferably added to the reaction zone, an excess of either reactant up to a mol ratio of about 1:5 can be employed. Usually, however, the mol ratio of lactam to phenolic compound is between 2:1 and 1:4.

The reactants can be contacted in the presence or absence of a solvent. When both reactants are liquid, they can be directly mixed in the reaction zone. However, in cases where no solvent is employed and one, or both, of the reactants is in the solid state, the solid material is heated above its melting point before obtaining the liquid mixture in which reaction takes place. The heating of the solid material can be accomplished by applied heat or by adding the solid or liquid reactant or a solution of a reactant which is maintained at a temperature above the melting point of the solid.

Alternatively, the lactam and phenolic reactants may be contacted in a solvent which may be maintained at a temperature above the melting temperature of the reactants. Specifically, the components of the reaction can be admixed by first forming a separate solution of each and gradually adding the solutions to the reactor or each of the components in the same solvent may be separately added to the reactor. The concentration of each component in the solvent or dispersant is from about 1% by weight up to the saturation limit of the liquid. Suitable solvents for both the phenolic compound and the lactam species include carbon tetrachloride, chloroform, water, benzene, xylene, toluene, chlorohexane, heptane, isooctane, acetic acid, etc. and mixtures thereof. The reaction solution can also include a stabilization agent, such as for example, chloroform in a concentration of from 0.5 to 8% by weight or higher.

After the complex is formed, which is usually marked by an exotherm or an exothermic rise in the temperature of the liquid in the reaction zone, the reactor is cooled, by allowing to cool gradually, by rapid cooling or by flash chilling, generally to a temperature between about 40° and about 5° below the reaction temperature or the temperature at which the solid or crystalline product is formed. In cases where a solvent is used, it is then removed by decantation and/or evaporation. The product is washed at a temperature between about 0° C and about 60° C with a suitable liquid, such as eg. hot water, and the wash liquid removed. The product may be recrystallized by warming it in solvent until dissolved and then cooling. This procedure can be repeated as often as necessary to achieve the desired purity of the complex product. In some cases, when crystals are not formed with normal cooling, it may be desirable to cool the product liquid mixture to significantly lower temperatures, eg. down to about −40° C in order to initiate the crystalline state.

In regard to the reaction and subsequent separation and washing procedure, it is to be considered most surprising that the complexes are stable to hot solvents, in particular to hot water. In fact, many of the complexes formed in accordance with the invention could be crystallized out of water with no decomposition of the complex occurring.

Instances of suitable substituted monohydroxy phenols for use in accordance with the invention include o-, m- and p- cresol, 3,4-dichlorophenol, 2,4,5-trichlorophenol, o-, m- and p-bromophenol, 4-chloro-2, 5-dimethylphenol, 4-cyanophenol, 4-nonylphenol, 3-ethoxyphenol, 2,6-dimethoxyphenol, L-Dopa, 4-ethylphenol, 4-pentylphenol, thymol, and including those of the following Examples.

Examples of suitable lactams include N-cyclohexyl-2-pyrrolidone, N-octyl-2-pyrrolidone, 2-pyrrolidone, e-caprolactam, N-methyl-2-pyrrolidone and the like, including those of the following Examples.

The compounds in accordance with the invention have proved to be suitable for use as germicides. In most instances the phenolic moiety of the complex compounds is detoxified, whereas, in their uncombined state, these phenols, although excellent germicides in themselves, are frequently quite toxic and irritating to the skin. The detoxification takes place in part due to slow release of the phenol.

It has also been found that the complexes of the invention can be used as deodorants. They are also suitable in dye applications acting as dye carriers for polyester fibers, etc. It has been found advantageous to use the complexes in accordance with the invention to avoid the result where chlorinated phenols are used such concentrations that bodies of water are polluted thereby. Thus, the complexes of the substituted monohydroxy phenols and the lactams of the invention can be used to detoxify such phenols and to purify drinking water from lakes and rivers.

The complexes are also suitable for use in plasticizers, such as dibutyl phthalate, dimethyl phthalate, and cetyl palmitate for preventing the formation of mould. Additionally, these complexes have been found to be particularly useful as antioxidants. The complexes result in a reduced or minimal vapor pressure of the phenol involved, thus resulting in greater persistence in application and less odor and drifting of the medicament in connection with which they are used. It is also advantageous for the complexes of the invention to be used in the agricultural field in that they have been found to release agricultural chemicals at a controlled rate, i.e. release of a phenol as in a time-controlled fertilizer, weed killer, bactericide, herbicide, fungicide, etc. Thus, the complexes in accordance with the invention may be used in admixture with fertilizers, soil sterilants, insecticides, larvicides, arachidicides, nematocides, herbicides and the like, providing for release over greater periods and for prolonged effect with respect to retarded leaching of the active agent in connection with which they are used.

More specific illustrations of the usefulness of the compounds of the invention are the incorporation thereof into calamine lotion or into vanishing cream, face cream, hexachlorophene, isopropanol as antiitching agents, as an antioxidant in slushing oils, hydraulic fluids and lube oils, as an additive in a protective thermoplastic coating for metals, as an active agent in germicidal compositions, as anti-rancidity agents for edible fats, as anti-gas fading agents for dyed cellulose acetate fibers and as films, stabilizing agents for monomers, rubber antioxidants, and the like.

Fungicidal compositions can be prepared by reacting N-methylpyrrolidone and pentachlorophenol to provide the 1:2 complex

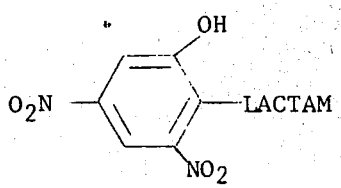

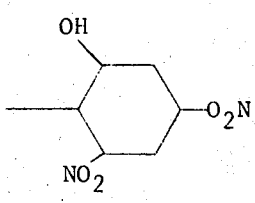

which, in an aqueous slurry of about 2% Igepal (polyethroxylated hydrophobe manufactured by GAF) can be atomized and used as a fungicidal spray.

A herbicidal composition of N-methylpyrrolidone and perchlorophenol

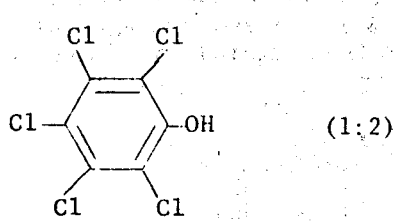

when incorporated in a concentration of from about 1 to 10% by volume in oil, is also useful as a wood preservative as well as a weed killer.

The complex compounds of this invention are usually employed in the above applications by dispersing the complex in a suitable inert carrier or solvent such as sawdust, attapulgite clay, kaolin, montmorillonite, talc, fuller's earth, diatomaceous earth, silica, wood flower, walnut shell meal, pulverized oak leaves, water, glycerine, petroleum, mineral or pale oils, Igepal, beeswax base, vaseline, hexachlorophene, isopropanol, benzene toluene, xylene, cyclohexane, etc. or any of the solvents mentioned in the following examples or mixtures thereof, and are employed in concentration therein between about 0.05% and 25% by weight depending upon the field of application and the effective amount desired. Generally, the present complex compounds are incorporated with a carrier or in a standard formulation by admixing therewith, preferably at a temperature between room temperature and about 130° C until a uniform mixture is obtained. This invention will appear more fully from the examples which follow. These examples are set forth by way of illustration only, and it will be understood that the invention cannot be construed as limited in spirit or in scope by the details contained therein and that other species listed above can be substituted in the following examples to provide the corresponding lactam-substituted phenol (1:2) complexes which are useful in the above described applications. All values in the following examples are by weight unless otherwise indicated.

EXAMPLE 1

PREPARATION OF N-METHYL-2-PYRROLIDONE COMPLEX WITH 2,4,5-TRICHLOROPHENOL (1:2)

A complex consisting of 2 mols of the phenol and 1 mol of N-methyl-2-pyrrolidone was prepared by admixing 0.10 mol (19.85g) 2,4,5-trichlorophenol and 0.05 mol (4.95 g) N-methyl-2-pyrrolidone and warming the mixture to 80° C until a clear liquid was obtained. On cooling the mixture to room temperature, a solid product was formed. The product was crystallized out of n-heptane and yielded a solid melting at 49°–51° C.

Elemental analysis gave the following results:

|    | Calculated | Found  |
|----|------------|--------|
| C  | 41.1%      | 40.70% |
| H  | 3.44       | 3.19   |
| N  | 2.82       | 2.73   |
| Cl | 42.60      | 42.69  |

EXAMPLE 2

PREPARATION OF N-METHYL-2-PYRROLIDONE COMPLEX WITH 4-NITROPHENOL (1:2)

A mixture of 0.2 mol (27.8 g) 4-nitrophenol and 0.10 mol (9.4 g) N-methyl-2-pyrrolidone was heated to 120° C. Prior to initiating the heating, a slight exotherm was noted indicating a complex had been formed. On cooling, a solid was obtained which melted at 101°–112° C. Attempted crystallization from ionic solvents broke up the complex which appeared to be less stable than any of the previously described complexes.

Additional relatively unstable complexes were prepared from p-phenyl-phenol, 1-hydroxyanthraquinone, and p-amino phenol each with N-methyl-2-pyrrolidone. However, the stability of these complexes may be improved by flash chilling to crystallize and the addition of a stabilizer.

When morpholone and hydroquinone were subjected to the same treatment, no complex was formed.

EXAMPLES 3 THROUGH 11

The following examples in Table I are provided to illustrate species of complex substituted monohydroxy phenol - lactam -substituted monohydroxy phenol complexes within the scope of the present invention. In the following, the designated amounts of N-methyl-2-pyrrolidone and substituted monohydroxy phenolic compound are generally added to a glass reaction vessel with stirring until a homogeneous mixture is obtained. The vessel is maintained at a relatively low temperature between about 20° C and about 120° C and the occurrence of an exotherm marks the formation of the complex. The heating is then discontinued and the mixture is held in the vessel for about one hour to insure completion of reaction. After cooling about 20° to 70°, the formed solid product is dissolved in toluene and cooled until the crystals reappear. The toluene is then removed, the product washed with warm water and then dried to recover product complex.

While the complex products of the present invention display reasonably good activity in the applications discussed above, they are most particularly useful in the applications reported in the following Table I in the concentrations set forth therein.

monohydroxy phenolic moiety is mono-, di-, or tri-substituted.

3. The crystalline complex of claim 2 wherein the monohydroxy phenolic moiety is substituted with halogen, alkoxy of 1 to 3 carbon atoms, cyano, or alkyl of 1 to 6 carbon atoms.

4. A complex according to claim 1 designated N-methyl-2-pyrrolidone - 2,4,5-trichlorophenol.

5. A complex according to claim 1 designated N-

TABLE I

| Ex. No. | Mols NMP (1) | Mols Phenolic Compound | Reactor Temp. °C | Ratio MP:P | Character of Complex | Applications (2) (concentrations employed % by weight of complex in carrier) | | | | | | | |
|---|---|---|---|---|---|---|---|---|---|---|---|---|---|
| | | | | | | G | I | H | W | P | A | C | R | S |
| 3 | 1 | 2 of pentachlorophenol | 120 | 1:2 | cryst. | | | | | | | | 0.1 to 5 | |
| 4 | 1 | 2 of 3,5-dinitrophenol | 128 | 1:2 | cryst. | 0.8 to 3 | | | | | | | | |
| 5 | 1 | 2 of 4-cyanophenol | 105 | 1:2 | cryst. | 0.01 to 1 | | | | | | | | |
| 6 | 1 | 2 of 2,4-dimethylphenol | 95 | 1:2 | cryst. | | | | | 1-10 | 2-5 | | | |
| 7 | 1 | 2 of 4-cyclohexylphenol | 140 | 1:2 | cryst. | 0.5-5 | | | | | 2-5 | | | |
| 8 | 0.05 | 0.1 of 2,4,5-trichlorophenol | 80 | 1:2 | cryst. | | | 0.1 to 10 | 2-5 | | 2-5 | | | 0.5 to 10 |
| 9 | 0.1 | 0.2 of 2,4,6-trinitrophenol | 120 | 1:2 | cryst. | | | | | | | 1 to 10 | | |
| 10 | 1 | 2 of 2,6-dibromo-4-cyano phenol | 145 | 1:2 | cryst. | 0.05 to 5 | | | | | | | | |
| 11 | 1 | 2 of 4-butyl phenol | 130 | 1:2 | cryst. | 0.5 to 5 | | | | | 1-8 | | | |

(1) N-methyl-2-pyrrolidone
(2) In the above table, G = germicide; I = insecticide; H = herbicide; W = wood preservative; P = plasticizer; A = antioxidant; R = Fungicide; C = carrier for dyes; P = plant growth repellent and S = skin emollient.

We claim:

1. A low molecular weight crystalline lactam monohydroxy phenol complex having the following formula

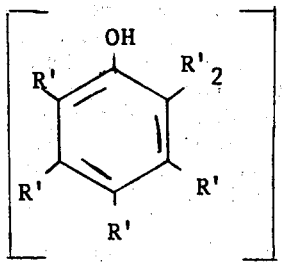 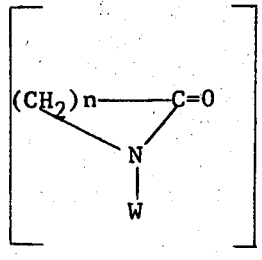 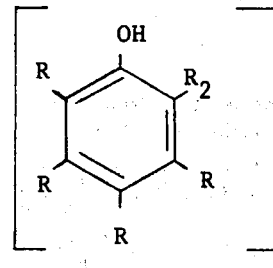

wherein $n$ is an integer of 3 to 5; W is hydrogen or alkyl having from 1 to 8 carbon atoms including cycloalkyl substituents; each R, R', $R_2$ and $R'_2$ is hydrogen, halogen, alkyl having from 1 to 12 carbon atoms, alkoxy of from 1 to 3 carbon atoms, nitro, or cyano and at least one R, R', $R_2$ and $R'_2$ is a substituent other than hydrogen; and wherein $R_2$ and $R'_2$ can also be alaninyl.

2. The crystalline complex of claim 1 wherein the methyl-2-pyrrolidone - 2,4-dimethylphenol.

6. A complex according to claim 1 designated N-cyclohexyl-2-pyrrolidone - 2-ethylphenol.

7. A complex according to claim 1 designated N-methyl-2-pyrrolidone - 2,4,6-trinitrophenol.

8. A complex according to claim 1 designated N-methyl-2-pyrrolidone - pentachlorophenol.

9. A complex according to claim 1 designated N-methylpyrrolidone - 2,6-dibromo-4-cyanophenol.

10. A complex according to claim 1 designated N-methyl-2-pyrrolidone - 4-cyanophenol.

* * * * *